United States Patent
Cosmescu

(10) Patent No.: US 10,390,875 B2
(45) Date of Patent: Aug. 27, 2019

(54) SYSTEM AND APPARATUS FOR AUTOMATIC ACTIVATION USING RADIO FREQUENCY SENSOR

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 268 days.

(21) Appl. No.: 14/791,015

(22) Filed: Jul. 2, 2015

(65) Prior Publication Data

US 2016/0000494 A1 Jan. 7, 2016

Related U.S. Application Data

(60) Provisional application No. 62/020,016, filed on Jul. 2, 2014.

(51) Int. Cl.
*A61B 18/12* (2006.01)
*A61B 18/00* (2006.01)
*A61B 17/00* (2006.01)

(52) U.S. Cl.
CPC .......... *A61B 18/1206* (2013.01); *A61B 18/12* (2013.01); *A61B 2017/00221* (2013.01); *A61B 2018/00702* (2013.01); *A61B 2018/00779* (2013.01); *A61B 2218/008* (2013.01)

(58) Field of Classification Search
CPC .......... A61B 2017/00221; A61B 18/12; A61B 18/1206; A61B 2018/00702; A61B 2018/00708; A61B 2018/00779; A61B 2218/008; A61B 2018/00928; A61B 2018/00886; A61B 2018/00785; A61B 2017/00039

See application file for complete search history.

(56) References Cited

U.S. PATENT DOCUMENTS

| | | | | |
|---|---|---|---|---|
| 3,500,898 A * | 3/1970 | Gerhart, Jr. | ............ | G05D 23/24 165/256 |
| 4,493,191 A * | 1/1985 | Hanson | ................ | B60H 1/3232 340/588 |
| 5,318,516 A * | 6/1994 | Cosmescu | .......... | A61B 18/1402 604/35 |
| 5,674,219 A * | 10/1997 | Monson | ............. | A61B 18/1402 604/22 |
| 2008/0167671 A1* | 7/2008 | Giordano | ......... | A61B 17/07207 606/167 |
| 2009/0259220 A1* | 10/2009 | Appling | ................. | A61B 18/22 606/10 |

FOREIGN PATENT DOCUMENTS

GB 1437770 A * 6/1976 ............ F02P 3/0435

* cited by examiner

*Primary Examiner* — Jaymi E Della
*Assistant Examiner* — Sean W Collins
(74) *Attorney, Agent, or Firm* — Zeman-Mullen & Ford, LLP

(57) ABSTRACT

A system and apparatus for automatic smoke evacuation using an RF sensor. The system and apparatus utilizes an RF sensor for automatic activation of an evacuator that evacuates smoke and/or debris during the use of any electrosurgical instrument or surgical instrument that is capable of generating smoke and/or debris and capable of producing a radiofrequency during its operation. Exemplary embodiments of the system and apparatus for automatic smoke evacuation include both wired and wireless embodiments.

10 Claims, 5 Drawing Sheets

SYSTEM AND APPARATUS FOR AUTOMATIC ACTIVATION USING RADIO FREQUENCY SENSOR

CROSS-REFERENCE TO RELATED APPLICATIONS

This application claims priority to provisional patent application having Ser. No. 62/020,016, filed Jul. 2, 2014, which is herein incorporated by reference in its entirety.

FIELD OF INVENTION

The present invention is generally directed to a system and apparatus for automatic activation using a radio frequency (RF) sensor. More particularly, the present invention is directed to a system and apparatus that utilizes an RF sensor for automatic activation of an evacuator that evacuates smoke and/or debris during the use of any electro surgical instrument or surgical instrument that is capable of generating smoke and/or debris.

BACKGROUND OF THE INVENTION

Many surgical procedures using electrosurgical devices and/or instruments produce unwanted smoke and debris that must be removed from the surgical site. As a result, many smoke evacuation systems and devices have been created to assist in removing this smoke and debris. Some of those systems and devices provide for automated removal of the smoke and debris.

In the present invention, there are two exemplary embodiments of the system and apparatus for automatic smoke activation using a radiofrequency sensor. One exemplary embodiment utilizes an RF sensor and transmitter that can be directly connected to a smoke evacuation unit via a wired/electrical cord connection. The other exemplary embodiment utilizes a wireless RF sensor and transmitter and a separate receiver that can be connected to, or positioned within, a smoke evacuation device.

The wireless RF sensor and transmitter of the second exemplary embodiment can be placed anywhere within the operating room/environment. The RF sensor and transmitter of the first exemplary embodiment and the wireless RF sensor and transmitter of the second exemplary embodiment capture a wide range of radio frequency waves created by the operation of a multitude of electrosurgical/surgical instruments that are powered via an energy source. In addition, the RF sensor and transmitter of the first exemplary embodiment and the wireless RF sensor and transmitter of the second exemplary embodiment can be positioned anywhere within the operating room/environment thereby making it easier for the physician or surgeon to utilize the electrosurgical/surgical instruments along with automated smoke/debris evacuation without encumbering the operating area of the surgeon/physician with obtrusive equipment and/or machines.

The increased RF sensitivity and extensive placement/positioning options of the RF sensor and transmitter and wireless RF sensor and transmitter of the exemplary embodiments of the invention are improvements over prior RF sensors used in the field. These improvements are achieved with limited components/elements that comprise the wired and wireless exemplary embodiments of the present invention thereby providing an effective, efficient, and cost efficient means for providing automated smoke evacuation with any electrosurgical instrument or surgical instrument that utilizes and/or emits RF energy during its operation. Examples of such electrosurgery instruments and surgical instruments include, but are not limited to, electrosurgery pencils, electrosurgery blades, harmonic scalpels, tissue sealers, electrosurgical forceps, electrosurgical tips, ultrasonic devices, and any other electrosurgical instrument or surgical instrument that utilizes and/or emits RF waves (including low RF waves and high RF waves; i.e. a wide range of RF waves that covers all RF waves created during use of any of the electrosurgical/surgical instruments) during operation or employment of the instrument.

SUMMARY OF THE INVENTION

The present invention is directed to a system for automatic smoke evacuation of smoke and debris from a surgical site during the use of any surgical instrument that is capable of producing a radiofrequency during its operation. In one exemplary embodiment, the automatic smoke evacuation system of the present invention includes a surgical instrument capable of producing a radiofrequency during its operation, a smoke evacuation unit capable of evacuating smoke and/or debris through a smoke evacuation channel or tubing, and a radiofrequency sensor connected to the smoke evacuation unit that is capable of sending a signal to the smoke evacuation unit where the radiofrequency sensor includes at least two transistors in sequence.

The radiofrequency sensor may also include an optocoupler in sequence with at least one of the two transistors. The radiofrequency sensor may further include a relay that is activated by the optocoupler and a switch that is operated by the relay where the switch is capable of sending a signal to the smoke evacuation unit. The radiofrequency sensor may also include at least one resistor between the two transistors. Further, the surgical instrument capable of producing a radiofrequency during its operation may include one or more of an electrosurgery pencil, an electrosurgery blade, a harmonic scalpel, a tissue sealer, an electrosurgical forceps, an electrosurgical tip, and an ultrasonic device.

In another exemplary embodiment, the automatic smoke evacuation system of the present invention includes a surgical instrument capable of producing a radiofrequency during its operation, a smoke evacuation unit capable of evacuating smoke and/or debris through a smoke evacuation channel or tubing, a wireless radiofrequency sensor and transmitter that is capable of receiving a signal from the surgical instrument and transmitting a signal, and a radiofrequency receiver connected to, or incorporated within, the smoke evacuation unit that is capable of receiving a signal transmitted from the wireless radiofrequency sensor and transmitter. The wireless radiofrequency sensor and transmitter include a plurality of radiofrequency sensor components and a plurality of radiofrequency transmitter components. The plurality of radiofrequency sensor components may include at least two transistors in sequence. The plurality of radiofrequency sensor components may also include an optocoupler in sequence with at least one of the two transistors. The plurality of radiofrequency sensor components may further include a relay that is activated by the optocoupler and a switch that is operated by the relay.

The plurality of radiofrequency transmitter components of the wireless radiofrequency sensor and transmitter may include a microcontroller capable of receiving a signal from the switch of the sensor components and a radio transmitter capable of sending a signal to the radiofrequency receiver. The radiofrequency receiver may include a radio receiver in sequence with a microcontroller which operates a relay that activates a switch that sends a signal to the smoke evacuation unit. The radiofrequency receiver may also include at least one capacitor and a crystal oscillator.

The wireless radiofrequency sensor and transmitter of the second exemplary embodiment of the automatic smoke evacuation system of the present invention may include a first antenna for receiving a radiofrequency signal form the surgical instrument and a second antenna for transmitting a signal to the radiofrequency receiver. The radiofrequency receiver may include a third antenna for receiving the signal form the second antenna. The surgical instrument of the second exemplary embodiment of the automated smoke evacuation system of the present invention that is capable of producing a radiofrequency during its operation may include one or more of an electrosurgery pencil, an electrosurgery blade, a harmonic scalpel, a tissue sealer, an electrosurgical forceps, an electrosurgical tip, and an ultrasonic device.

BRIEF DESCRIPTION OF THE DRAWINGS

The subject invention will hereinafter be described in conjunction with the appended drawing figures, wherein like numerals denote like elements.

DETAILED DESCRIPTION

Figure 1:
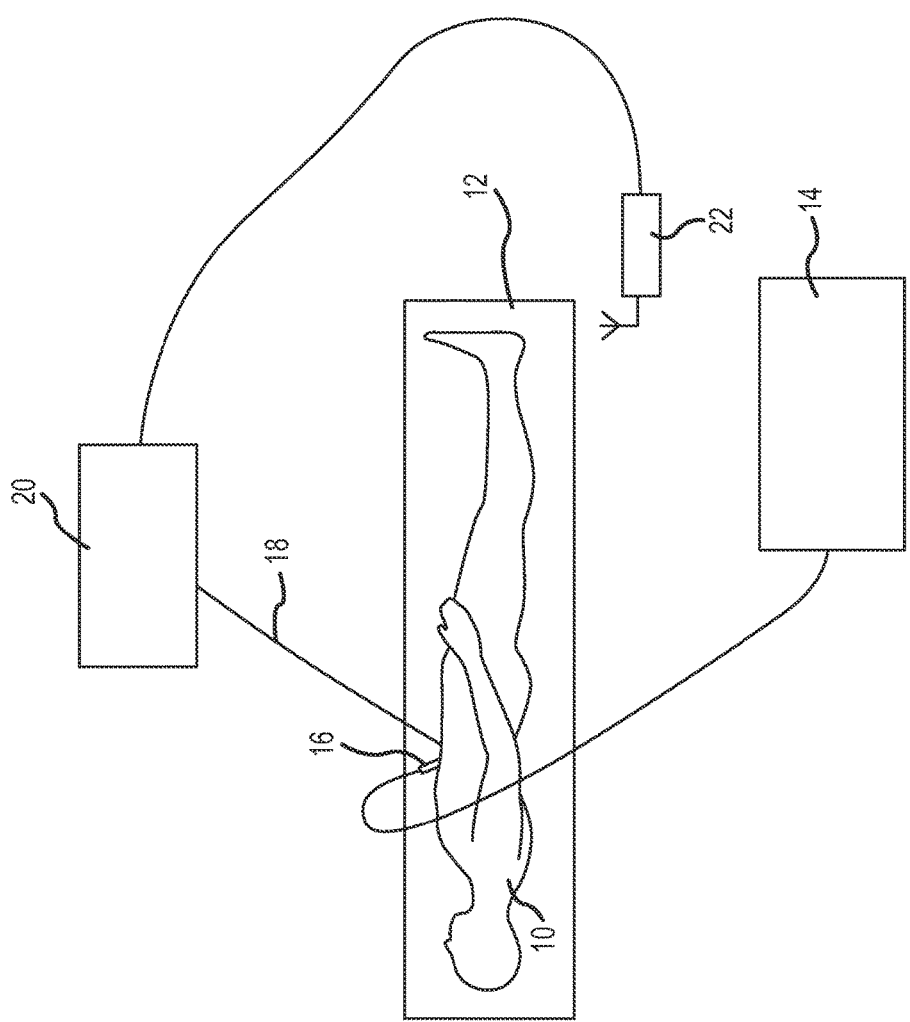
FIG. 1 is a block diagram of one exemplary embodiment of the automatic activation system using an RF sensor according to the present invention.

The automatic smoke evacuation system using RF sensor of the present invention is generally directed to exemplary embodiments which utilize a radiofrequency sensor having increased sensitivity that is capable of detecting radiofrequencies produced by surgical instruments and sending a signal to a smoke evacuation unit to activate smoke evacuation when the surgical instruments are being utilized or operated. FIG. 1 is a block diagram of one exemplary embodiment of the automatic activation system using an RF sensor according to the present invention. The automatic smoke evacuation system using RF sensor of the present invention is utilized when performing surgical procedures on a patient 10 placed on an operating surface 12 using a surgical instrument 16 that is capable of producing a radiofrequency during its operation. Surgical instrument 16 may be powered by an electrosurgery unit 14. A smoke evacuation channel or tubing 18 is connected to a smoke evacuation unit 20 for removing smoke and/or debris from the surgical site while operating the surgical instrument 16. A radiofrequency sensor 22 with increased sensitivity for sensing radiofrequencies produced by surgical instrument 16 is connected to smoke evacuation unit 20.

Figure 2:
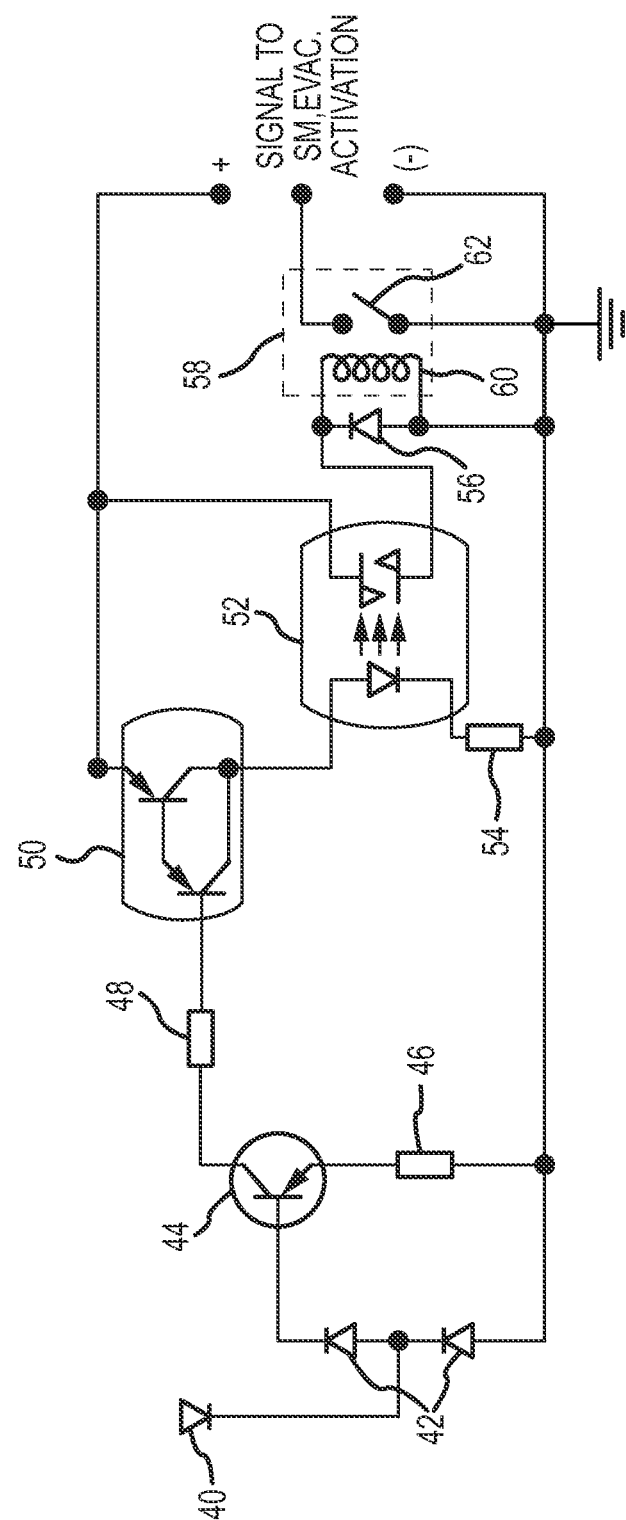
FIG. 2 is an exemplary embodiment of an electrical schematic of the RF sensor apparatus with increased sensitivity shown in FIG. 1.

FIG. 2 is an exemplary embodiment of an electrical schematic of the RF sensor apparatus with increased sensitivity shown in FIG. 1. RF sensor 22 includes an antenna 40 which receives an RF signal from the surgical instrument 16 that produces RF energy that is connected to diode 42 which receives RF signal form the antenna 40. Diode 42 is connected to two transistors 44, 50 connected in sequence and at least one of the transistors 44, 50 is connected to optocoupler 52. Transistor 44 amplifies and switches the RF signal and transistor 50 is a double transistor that amplifies or increases sensitivity of the RF signal. One or more resistors 46, 48, 54 may separate the transistors and the optocoupler to restrict the RF signal. Optocoupler 52 is connected to diode 56 which allows the RF signal to pass in one direction to relay 58 and relay coil 60. Relay 58 operates switch 62 by opening and closing the contacts of switch 62. When RF is produced by the surgical instrument 16, relay 58 closes the contacts of switch 62 and a signal is sent to the smoke evacuation unit 20 to activate the smoke evacuation unit 20.

Figure 3:
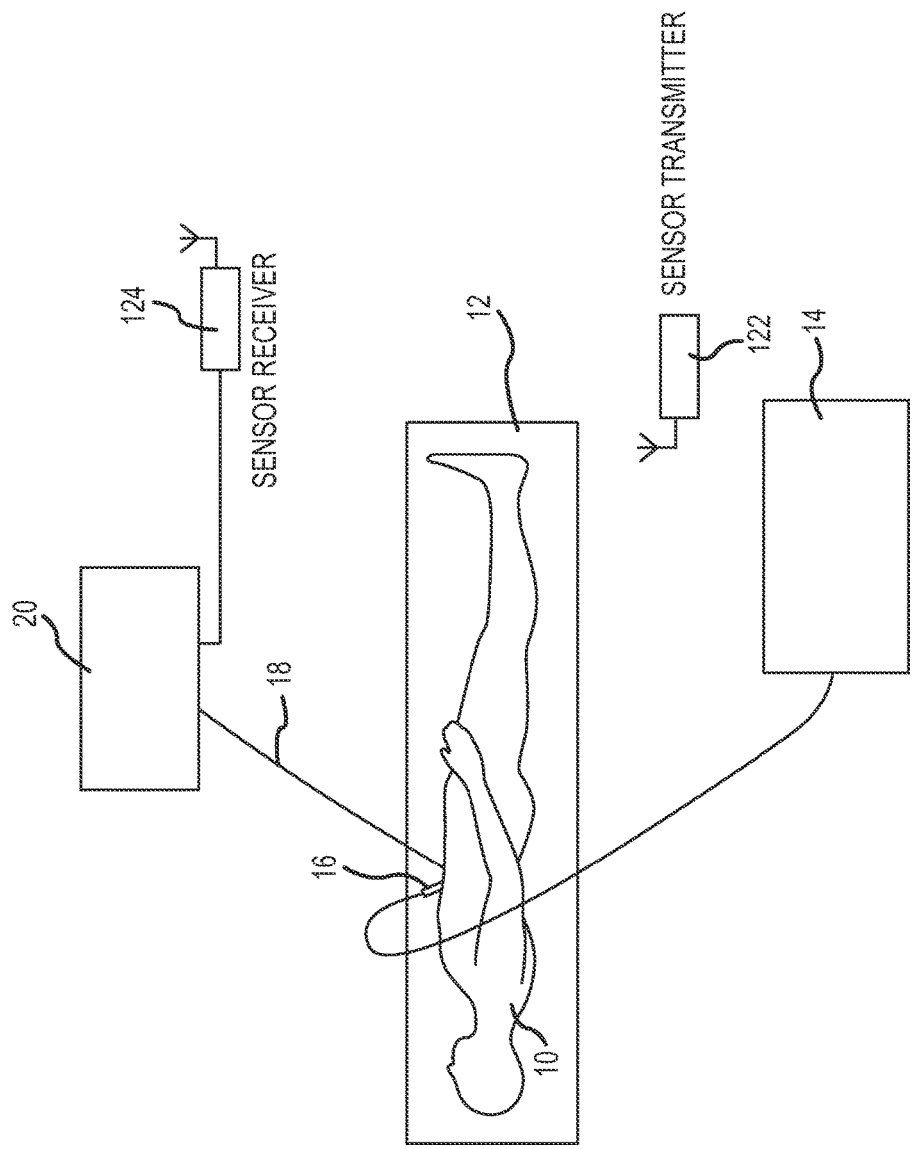
FIG. 3 is a block diagram of another exemplary embodiment of the automatic activation system using a wireless RF sensor according to the present invention.

A block diagram of another exemplary embodiment of the automatic activation system using a wireless RF sensor according to the present invention is shown in FIG. 3. The automatic smoke evacuation system using RF sensor of the present invention is utilized when performing surgical procedures on a patient 10 placed on an operating surface 12 using a surgical instrument 16 that is capable of producing a radiofrequency during its operation. Surgical instrument 16 may be powered by an electrosurgery unit 14. A smoke evacuation channel or tubing 18 is connected to a smoke evacuation unit 20 for removing smoke and/or debris from the surgical site while operating the surgical instrument 16. Wireless RF sensor and transmitter 122 can be placed anywhere within the operating room/environment. RF receiver 124 is connected to, or incorporated within, smoke evacuation unit 20 and is capable of receiving a signal transmitted from the wireless RF sensor and transmitter 122.

Figure 4:
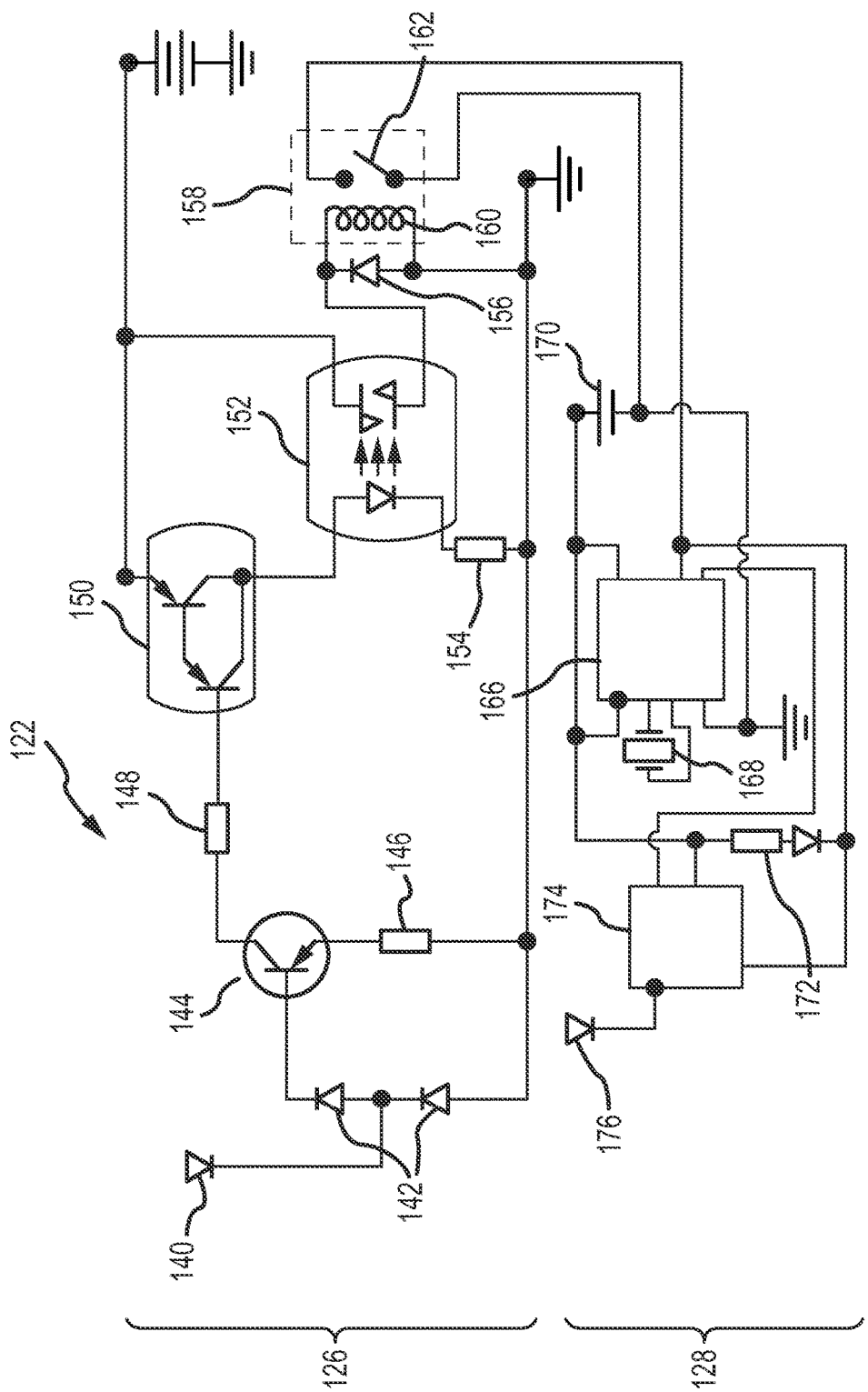
FIG. 4 is an exemplary embodiment of an electrical schematic of the wireless RF sensor and transmitter of the wireless RF sensor apparatus with increased sensitivity shown in FIG. 3.

FIG. 4 is an exemplary embodiment of an electrical schematic of the wireless RF sensor and transmitter of the wireless RF sensor apparatus with increased sensitivity shown in FIG. 3. The wireless RF sensor and transmitter 122 includes a plurality of RF sensor components 126 and a plurality of transmitter components 128. The plurality of sensor components 126 are configured like the RF sensor with increased sensitivity 22 shown in FIG. 2. The sensor components 126 include an antenna 140 which receives an RF signal from the surgical instrument 16 that produces RF energy that is connected to diode 142 which receives RF signal form the antenna 140. Diode 142 is connected to two transistors 144, 150 connected in sequence and at least one of the transistors 144, 150 is connected to optocoupler 152. Transistor 144 amplifies and switches the RF signal and transistor 150 is a double transistor that amplifies or increases sensitivity of the RF signal. One or more resistors 146, 148, 154 may separate the transistors and the optocoupler to restrict the RF signal. Optocoupler 152 is connected to diode 156 which allows the RF signal to pass in one direction to relay 158 and relay coil 160. Relay 158 operates switch 162 by opening and closing the contacts of switch 162. When RF is produced by the surgical instrument 16, relay 158 closes the contacts of switch 162 and a signal is sent to a microcontroller 166 which comprises one of the transmitter components 128. Microcontroller 166 is connected to crystal oscillator 168 and radio transmitter 174. Radio transmitter 174 is connected to antenna 176 which transmits a signal that is received by radiofrequency receiver 124 that is connected to or incorporated within smoke evacuation unit 120. Battery 170 powers transmitter components 128. Transmitter components 128 may also include one or more resistors 172.

Figure 5:
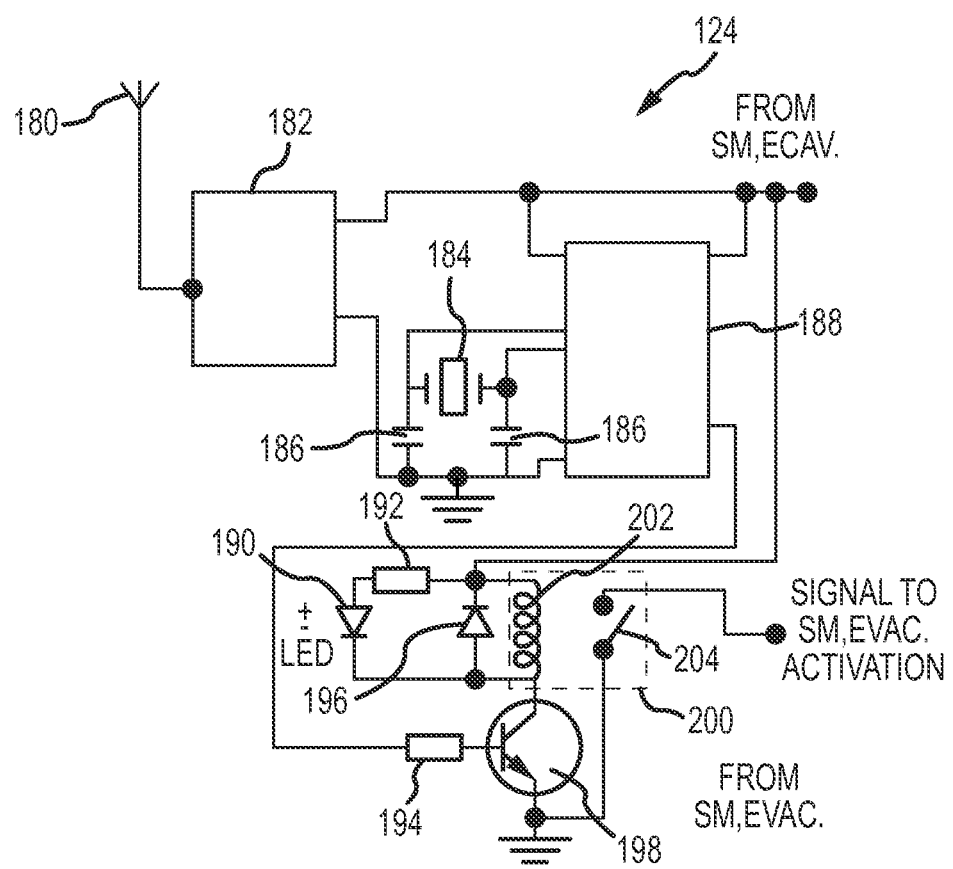
FIG. 5 is an exemplary embodiment of an electrical schematic of the radiofrequency receiver of the wireless RF sensor apparatus with increased sensitivity shown in FIG. 3.

FIG. 5 is an exemplary embodiment of an electrical schematic of the radiofrequency receiver of the wireless RF sensor apparatus with increased sensitivity shown in FIG. 3. The signal sent by antenna 176 and radio transmitter 174 is received by antenna 180 and radio receiver 182 of RF receiver 124. Radio receiver 182 is connected to microcontroller 188 which is connected to crystal oscillator 184 which uses mechanical resonance of a vibrating crystal of piezoelectric material to create an electrical signal with a very precise frequency. Capacitors 186 are connected to crystal oscillator 184 and are used to store electrical energy. Microcontroller 188 is connected to transistor 198 (which amplifies and switches RF signal) which is in turn connected to relay 200 and relay coil 202 which operate switch 204. Microcontroller 188 is also connected to diodes 190, 196 which are connected to relay 200. Resistors 192, 194 may also be included in the RF receiver 124. When a signal is received by antenna 180 of RF receiver 124, relay 200 closes contacts of switch 204 and a signal is sent to the smoke evacuation unit 20 to activate the smoke evacuation unit.

The above exemplary embodiments are not intended to limit the scope, applicability, or configuration of the invention in any way. Rather, the disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

It will also be understood by those skilled in the art that the scope of application for the wired and wireless embodiments of the RF sensor with increased sensitivity and RF sensor and transmitter with increased sensitivity used in combination with the RF receiver may go well beyond use with electrosurgical and surgical instruments and smoke evacuation. In other words, the wired and wireless RF sensors of the present invention could be used in other industry applications where it is important to be able to automate equipment that generates radio frequencies.

The invention claimed is:

1. A system for automatic smoke evacuation comprising:
   a surgical instrument capable of producing a radiofrequency during its operation;
   a smoke evacuation unit capable of evacuating at least one of smoke and debris through a smoke evacuation channel;
   a wireless radiofrequency sensor and transmitter device that is both separate from and not connected to the smoke evacuation unit and separate from and not contained within the surgical instrument, wherein the wireless radiofrequency sensor and transmitter device is capable of receiving a transmitter device signal from the surgical instrument and transmitting a signal;
   a radiofrequency receiver connected to, or incorporated within, the smoke evacuation unit that is capable of receiving the transmitter device signal transmitted from the wireless radiofrequency sensor and transmitter device,
   wherein the wireless radiofrequency sensor and transmitter device comprises a plurality of radiofrequency sensor components and a plurality of radiofrequency transmitter components, and
   wherein the plurality of radiofrequency sensor components includes a single transistor, a double transistor, and an optocoupler wherein the single transistor and the double transistor are in sequence with one another and the optocoupler is in sequence with the double transistor.

2. The automatic smoke evacuation system of claim 1 wherein the plurality of radiofrequency sensor components further includes a relay that is activated by the optocoupler and a switch that is operated by the relay.

3. The automatic smoke evacuation system of claim 2 wherein the plurality of radiofrequency transmitter components includes a microcontroller capable of receiving a signal from the switch and a radio transmitter capable of sending the transmitter device signal to the radiofrequency receiver.

4. The automatic smoke evacuation system of claim 3 wherein the radiofrequency receiver includes a radio receiver in sequence with a microcontroller which operates a relay that activates a switch that sends a signal to the smoke evacuation unit.

5. The automatic smoke evacuation system of claim 4 wherein the radiofrequency receiver further includes at least one capacitor and a crystal oscillator.

6. The automatic smoke evacuation system of claim 1 wherein the wireless radiofrequency sensor and transmitter device includes a first antenna for receiving the signal from the surgical instrument and a second antenna for transmitting the transmitter device signal to the radiofrequency receiver.

7. The automatic smoke evacuation system of claim 6 wherein the radiofrequency receiver includes a third antenna for receiving the transmitter device signal from the second antenna.

8. The automatic smoke evacuation system of claim 7 wherein the surgical instrument capable of producing a radiofrequency during its operation comprises at least one of an electrosurgery pencil, an electrosurgery blade, a harmonic scalpel, a tissue sealer, an electrosurgical forceps, an electrosurgical tip, and an ultrasonic device.

9. The automatic smoke evacuation system of claim 1 wherein the surgical instrument capable of producing a radiofrequency during its operation comprises at least one of an electrosurgery pencil, an electrosurgery blade, a harmonic scalpel, a tissue sealer, an electrosurgical forceps, an electrosurgical tip, and an ultrasonic device.

10. The automatic smoke evacuation system of claim 1 wherein the single transistor and the double transistor are separated by at least one resistor.

* * * * *